(12) United States Patent
Mahon et al.

(10) Patent No.: US 6,671,397 B1
(45) Date of Patent: Dec. 30, 2003

(54) MEASUREMENT SYSTEM HAVING A CAMERA WITH A LENS AND A SEPARATE SENSOR

(75) Inventors: James Mahon, Dublin (IE); Adrian Boyle, Kildare (IE); Niall Dorr, Dublin (IE); Peter Conlon, Dublin (IE)

(73) Assignee: M.V. Research Limited, Dublin (IE)

( * ) Notice: Subject to any disclaimer, the term of this patent is extended or adjusted under 35 U.S.C. 154(b) by 0 days.

(21) Appl. No.: 09/471,385

(22) Filed: Dec. 23, 1999

(30) Foreign Application Priority Data

Dec. 23, 1998 (IE) .................................................. 981009

(51) Int. Cl.[7] .................................................. G06K 9/00
(52) U.S. Cl. ................ 382/145; 250/559.46; 356/237.4
(58) Field of Search ................................. 382/145, 151, 382/141, 150, 146, 154; 348/126; 257/98; 250/559.44, 559.45, 559.46, 559.23, 559.34, 559.31; 356/237.4, 237.5; 702/40

(56) References Cited

U.S. PATENT DOCUMENTS

| | | | |
|---|---|---|---|
| 4,677,473 A | | 6/1987 | Okamoto et al. ............ 358/101 |
| 4,688,939 A | | 8/1987 | Ray ............................. 356/237 |
| 5,592,331 A | * | 1/1997 | Eastcott ....................... 356/394 |
| 5,838,434 A | * | 11/1998 | Skramsted et al. ......... 356/241.1 |
| 5,959,316 A | * | 9/1999 | Lowery ........................ 257/100 |
| 6,005,965 A | * | 12/1999 | Tsuda et al. ............ 250/559.08 |
| 6,219,442 B1 | * | 4/2001 | Harper et al. ................ 382/141 |

FOREIGN PATENT DOCUMENTS

EP 0638801 A1 2/1995

* cited by examiner

Primary Examiner—Leo Boudreau
Assistant Examiner—Shefali Patel
(74) Attorney, Agent, or Firm—Jacobson Holman PLLC

(57) ABSTRACT

A measurement system (1) has a camera with a lens (12) and a separate sensor (10) mounted so that their planes (13,11) intersect at an object plane (3) according to the Scheimpflug principle. A reference camera(4) is normal and provides a 2D normal image which is used by an image processor (25) to determine a calibration image. This allows the image processor to determine height of the object (2). A single image capture provides an image of the full object, such as a ball grid array (BGA).

7 Claims, 4 Drawing Sheets

MEASUREMENT SYSTEM HAVING A CAMERA WITH A LENS AND A SEPARATE SENSOR

FIELD OF THE INVENTION

The invention relates to measurement of size of objects in a high-throughput environment. An example is measurement of chip-scale package objects in an electronic circuit production environment.

PRIOR ART DISCUSSION

As electronic circuits and electronic integrated circuit packages become increasingly miniaturised the need for accurate measurement and control of parameters in the manufacturing environment becomes increasingly important in the reduction of defects and, ultimately, in the reduction of costs associated with that process. This is particularly true of ball placement in ball grid array, chip scale package and flip chip manufacturing.

In these processes the solder balls of a specified diameter are placed at a location on the copper pad of a packaged integrated circuit. Following the placement process the solder balls are attached to the substrate in a reflow process. The accuracy requirements in the position and height of the solder balls following this placement and reflow process depend on the specific dimensions of the package. In general. however, solder ball height and the relative heights of all the solder balls on a package is critical to the performance of the final package when it is in a functional position on a circuit board. For example, if one solder ball in a package is sufficiently far below the average height of all other solder balls it is likely that this ball will form an open circuit with the board at this location.

It is known to provide a system to measure x, y, and z positional and size data of a BGA using a two-camera "stereo" arrangement, as described in European Patent Specification No. EP0638801B1 (IBM). One camera is used to measure the centrality of a BGA and the other to sense the flatness. The flatness is measured by a tilted camera sensing crescent-shaped reflections from a light source located opposite the camera.

It appears that the accuracy which can be achieved for the height dimension is limited by variations in the sizes of the images reflected from the balls. Also, it appears that the throughput would not be as high as desirable because of the need to capture multiple images for each BGA. Also, capturing of multiple images (successive juxtaposed rows) for a single object requires sophisticated work table robotic control and image processing synchronisation.

OBJECTS OF THE INVENTION

One object of the invention is to provide for improved throughput in such systems.

Another object is to provide for improved accuracy.

SUMMARY OF THE INVENTION

According to the invention, there is provided a measurement system comprising means for supporting an object to be inspected in an object plane, a light source mounted to illuminate the object, an obliquely-mounted camera for capture of images of the illuminated object, and an image processor comprising means for determining height of the object according to measured offset from a calibration image, characterised in that, the camera comprises a sensor and a separate lens, and
the system further comprises means for supporting the sensor and the lens at mutually different angles whereby a plane through the sensor and a plane through the lens substantially intersect at the object plane according to the Scheimpflug principle to provide a relatively large field of view in focus.

In one embodiment, the system further comprises a reference camera mounted to capture a two-dimensional normal image of the object, and the image processor comprises means for determining the calibration image from said normal image.

In one embodiment, the light source is mounted with respect to the obliquely-mounted camera whereby the peak of the object is sensed.

In one embodiment, only an area including the peak of the object is sensed.

In one embodiment, the image processor comprises means for determining a centroid of the image to determine the peak of the object.

In one embodiment, the system further comprises a lateral light source arranged in an annular configuration with respect to the object support means to provide an annular image for the reference camera, and the image processor comprises means for determining the centroid of the annular image to provide the normal image.

In one embodiment, the obliquely-mounted camera comprises a filter to filter out light from the lateral light source, and the image processor comprises means for controlling simultaneous image acquisition from both the normal camera and the obliquely-mounted camera.

In one embodiment, the lateral light source comprises a ring of LEDs.

In another embodiment, the image processor stores reference data for a ball grid array and means for accepting or rejecting a ball grid array according to comparison of the measured height data and the reference data.

According to another aspect, the invention provides a method of inspecting an object comprising the steps of:

mounting a primary camera sensor and a lens over an object space so that they have non-parallel planes, mounting a reference camera over the object space, causing relative movement of the cameras and an object to a stationary position at which the primary camera lens plane, the primary camera sensor plane, and the object plane intersect according to the Scheimpflug principle, capturing a primary image of the full object at the primary camera and capturing a reference image of the full object at the reference camera without further relative movement of the cameras and the object, and an image processor determining a calibration image from the reference image, and determining height of the object according to a measured offset of the primary image from the calibration image.

In one embodiment, the object is a ball grid array.

In one embodiment, the object is illuminated with lateral light directed substantially parallel to the object plane whereby the reference image is annular, and the object is also illuminated by oblique light directed from an oblique angle whereby the primary image corresponds to a surface area only including an object peak.

In one embodiment, the lateral light and the oblique light have different wavelengths, light entering a camera is filtered to exclude the light for the other camera, and both the primary and the reference images are simultaneously captured.

DETAILED DESCRIPTION OF THE INVENTION

BRIEF DESCRIPTION OF THE DRAWINGS

The invention will be more clearly understood from the following description of some embodiments thereof given by way of example only with reference to the following drawings, in which.

DESCRIPTION OF THE EMBODIMENTS

Figure 1:
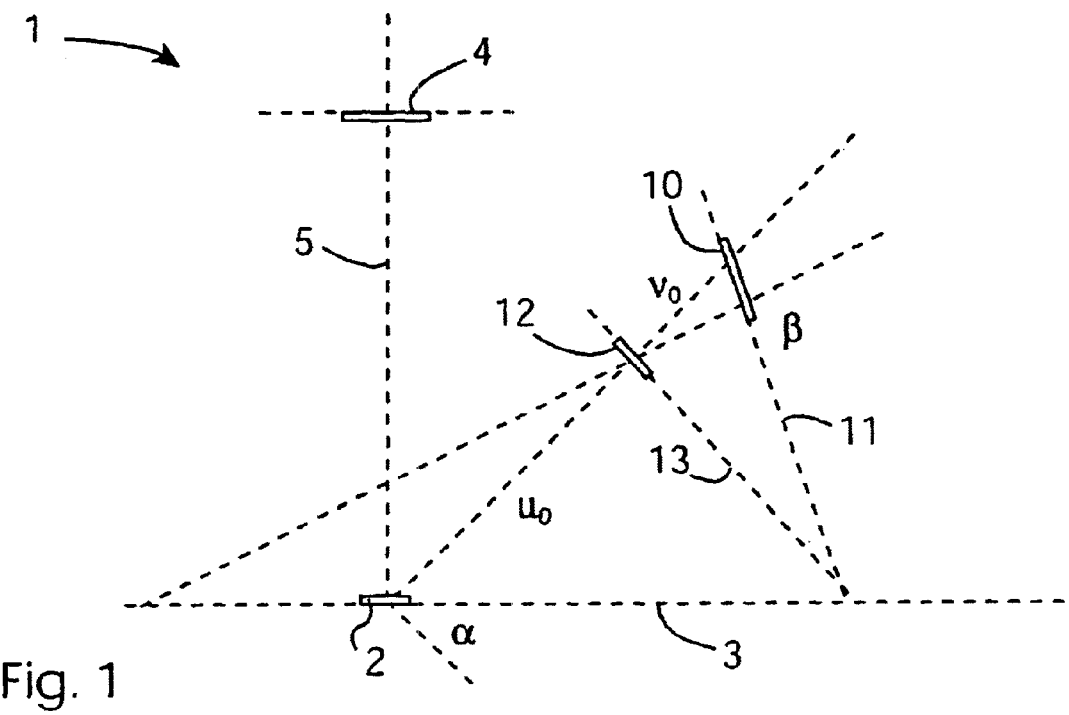
FIG. 1 is a diagrammatic representation of the optical scheme of a measurement system of the invention.
Figure 2:
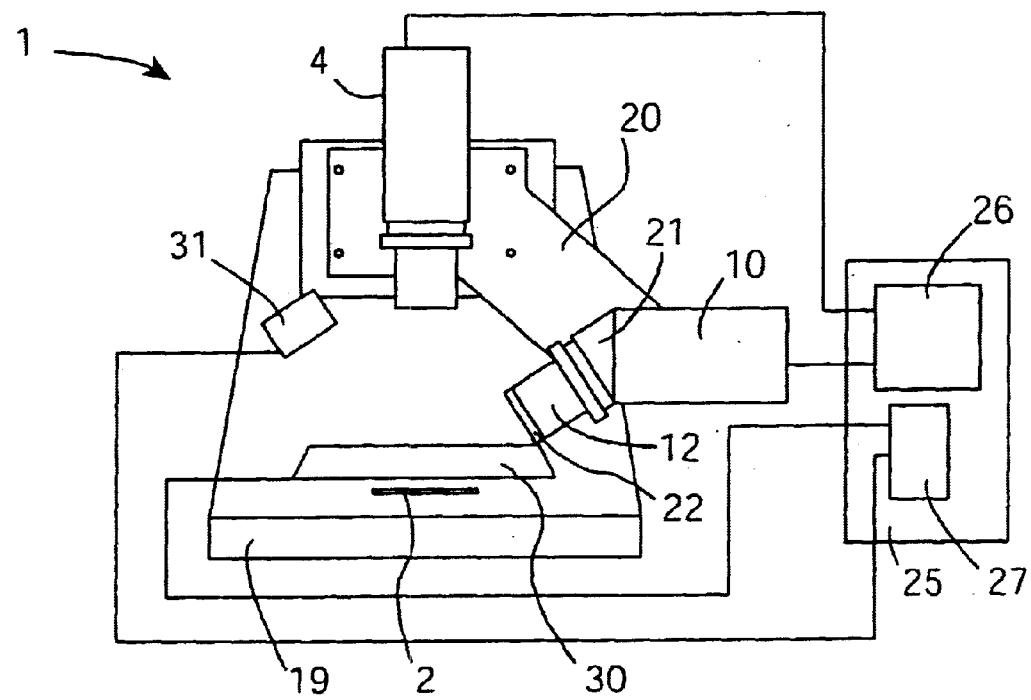
FIG. 2 is a schematic elevational view of the system.

Referring to FIGS. 1 and 2, a measurement system 1 comprises a table supporting an object 2 in an object plane 3, which in this embodiment is horizontal. A high resolution normal camera 4 is mounted at a position directly above the object 2 whereby an optical axis of the camera 4 intersects the object 2. A high resolution oblique camera comprises a sensor 10 in a plane 11, and a separate objective lens 12 in a plane 13. The planes 11 and 13 are not parallel and they intersect at the object plane 3, as shown in FIG. 1 to fulfill the Scheimpflug condition.

As shown in FIG. 2, the system 1 comprises a base 19 to provide a solid foundation for a table (not shown) mounted above a high-speed positioning system. A support framework 20 supports the normal camera 4, the sensor 10, and the lens 12. An adapter 21 interconnects the lens 12 and the sensor 10 to enforce the Scheimpflug principle and avoid loss of depth of field across the field of view. Alternatively, the objects to be inspected may be held stationary and the framework 20 may be mounted on a positioning system to allow location of both cameras above the stationary object.

A filter 22 is mounted in front of the lens 12 to allow separation of images due to different light sources and simultaneous image capture. An image processor 25 comprises a frame grabber 26 and a switching circuit 27 for the cameras and light sources. The switching circuit 27 allows simultaneous dual camera exposure through a shutter exposure or synchronised lighting strobe shutter exposure event.

The system further comprises a lateral light source 30 comprising a ring of LEDs mounted to direct light laterally (horizontally) towards the object 2. An oblique light source 31 comprises an array of LEDs mounted at an oblique angle to illuminate the peak of the object 2 with diffuse light, as described in more detail below.

The object 2 is in this embodiment an array of solder balls in a ball grid array, however, it may alternatively be a different type of solder deposit such as those for flip chip type electronic devices. Alternative applications include solder bumps such as those in bump grid arrays, pins such as in pin grid arrays, solder paste deposits at various process stages (pre and post re-flow), leads in leaded chip carriers, and 3D component profiles for components on circuit boards to confirm presence or absence.

Operation of the system 1 is based on determination of 2D coordinates using the normal camera 4 and 3D coordinate measurement using both cameras.

For the image sensed by the oblique sensor 10 to be in focus across the full field of view, it is essential that it is at an angle defined by the Scheimpflug condition (Equation 1), as follows:

$$\mathrm{Tan}\beta = \frac{v_0}{u_0}\mathrm{Tan}\alpha$$

Where β is the Scheimpflug angle, alpha is the angle between the optical axis of the sensor 10 and the object plane, and $v_0$ and $u_0$ are the image and object distances at the center of the object and image fields respectively. The central (axial) magnification, m, is defined by $m=v_0/u_0$.

Figure 3:
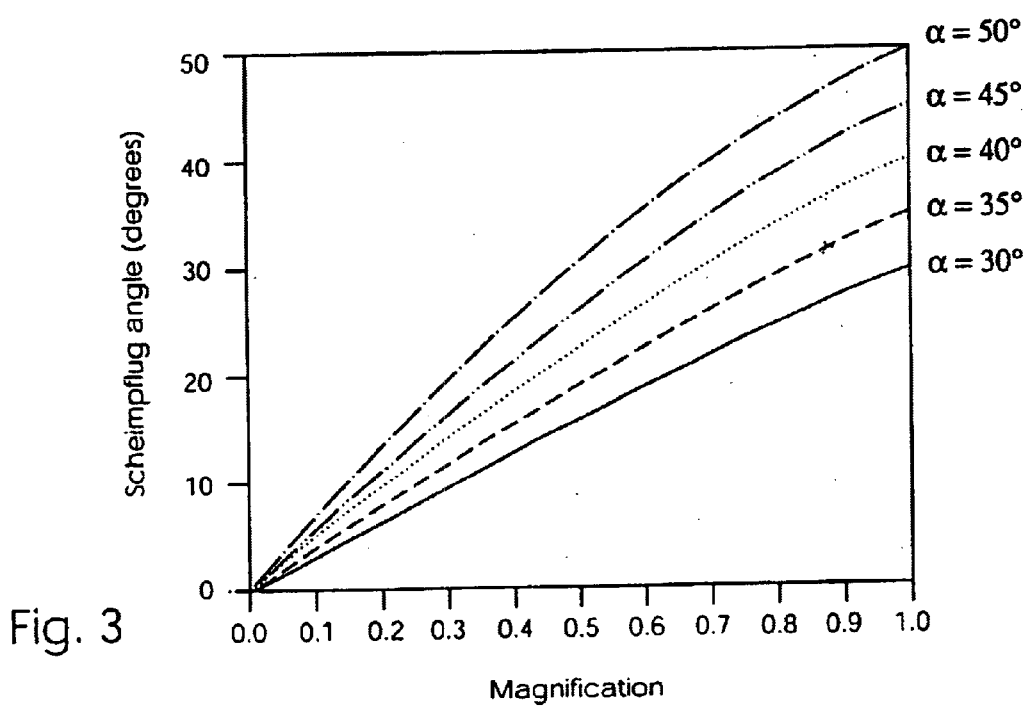
FIGS. 3 and 4 are plots illustrating variations of parameters in the system.
Figure 4:
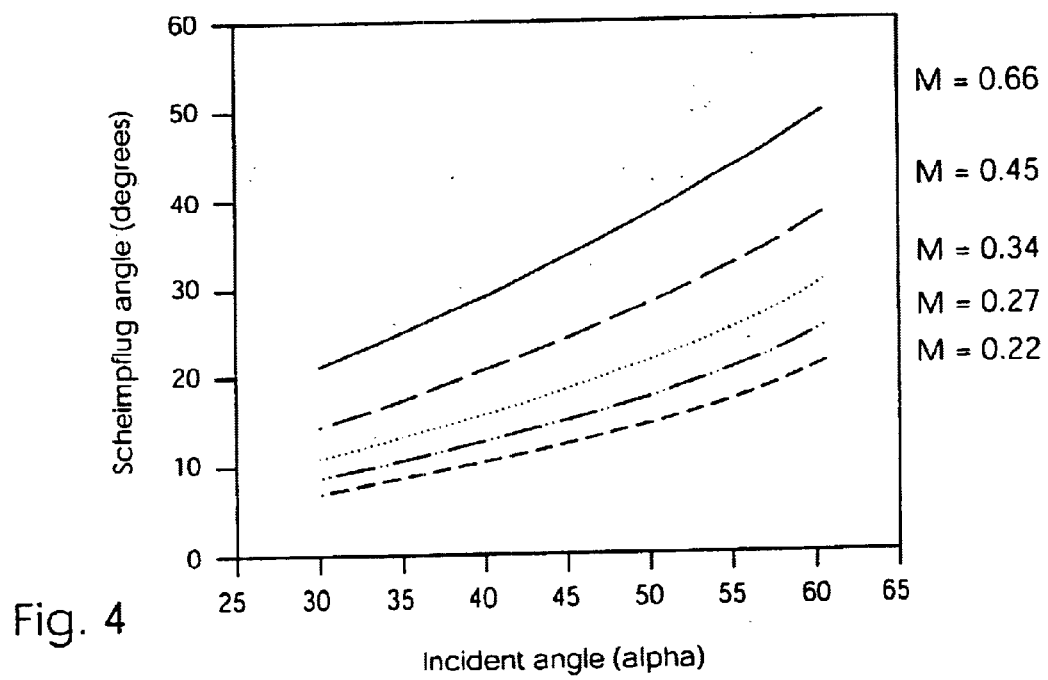

A graphical representation of the Scheimpflug angle as a function of nominal (axial) magnification for different viewing angles ranging from 30° to 50° is shown in FIG. 3. FIG. 4 shows a family of relationships for the required Scheimpflug angle at various magnifications for different values of alpha.

To ensure correct accuracy across the field of view, it is necessary to set the Scheimpflug sensor angle for the object field pixel size required, as the magnification changes slightly across the field of view. The amount of magnification variation depends on the axial (or nominal) magnification and the Scheimpflug angle. The relevance of these diagrams to the system 1 is that the choice of angle or lens magnification relate directly to the resolution and field of view of the object and so the angle and magnification must be chosen so that the required accuracy on the image plane can be achieved.

Figure 5:
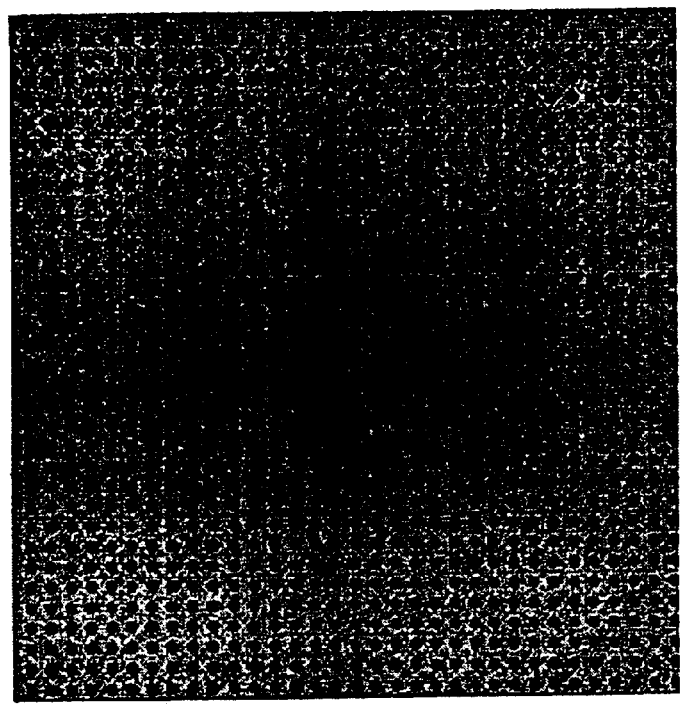
FIGS. 5 and 6 are sample two-dimensional normal and calibration views respectively.
Figure 6:
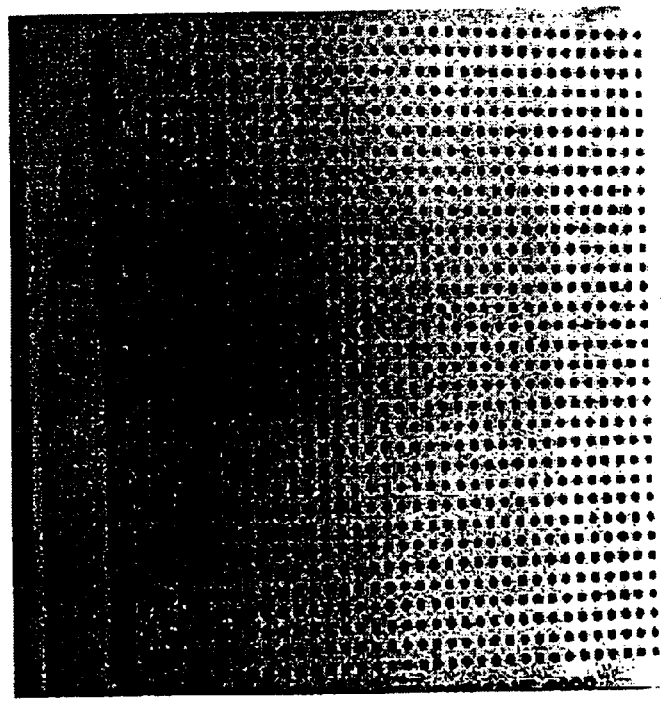

The image processor is calibrated by capturing a normal image of a two-dimensional calibration object as shown in FIG. 5, followed by an oblique view of the same object as shown in FIG. 6. This provides the image processor with the mappings or transforms between the two views without any third (height) dimension. In more detail, the calibration tool used in this process is a small piece of glass with a large number of dots printed on it. The dots are arranged as matrix of 38 by 38 dots of 0.2 mm diameter, which are 0.4 mm apart. During the calibration procedure, a digital image of the calibration tool is obtained from the normal camera 4. An example of this type of image is shown in FIG. 5. After processing this digital image, the location of all the dots is obtained. Then, the oblique sensor 10 is used to take a second image and the location of the dots will also be found in the image taken from this camera. An example of an image of the calibration tool obtained from the oblique camera is shown in FIG. 6. The image processor is programmed to match dots found in the image from the normal camera 4 with those found in the image from the oblique camera 10. Hence, each dot in the first image can be referenced to a corresponding dot in the second image. Then, using the mechanical stage, the entire optical structure supporting the cameras 4 and 10 is moved by a know distance H and the same operation will be repeated. Upon the completion of this step, the new locations of all the dots in both the image from the orthogonal camera and the image from the oblique camera will be known. Since the mechanical stage offers precise movement the location of the dots in the two images that were taken from the orthogonal camera will be identical. However, the location of the corresponding dots in the two images that were taken from the oblique camera will be different. This difference is extremely small in the horizontal direction in the image, but relatively substantial in the vertical direction. For ease of referencing, the shift or difference in the vertical location of the dots will be referred to as ZDIFF.

Using the following equation, one can obtain a calibration value (factor) for all the locations at which the dots were found in the images of the orthogonal camera.

$$\text{Calibration value } (x, y) = H/ZDIFF \qquad \text{Equation 2}$$

Where x and y correspond to the co-ordinates of the dot in the image taken from the orthogonal camera.

Equation 2 defines the reference plane from which all heights will be reported as well. This plane will be at H/2 from the top of the dots on the calibration tool.

Furthermore, the system records the location of the dots that were found in the images from the oblique camera in a Look-Up-Table (LUT). For the best results, the average (or mid-point) of the co-ordinates that were found is recorded. This LUT enables the system to provide an "expected location" in the image from the oblique camera for any point within the image obtained from the orthogonal camera. The LUT is a two-dimensional one that can be accessed by taking the XY co-ordinates of a point in the image from the orthogonal camera and indexing into this table.

Figure 7:
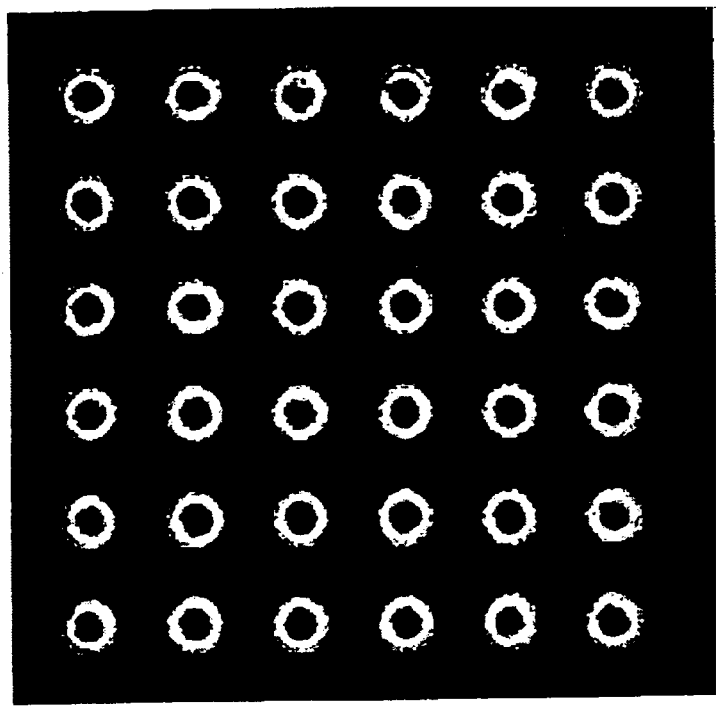
FIG. 7 is a sample image captured by a normal camera.

In operation, a normal view of the BGA is captured by the normal camera 4 and this has the pattern of the view of FIG. 5 because the height dimension is invisible in this view. The normal view is shown in FIG. 7. This includes an annulus for each ball because the BGA is illuminated from all angles in a lateral ring by the lateral source 30. The image processor uses this image to determine the geometric centroid using an edge detection and tracking algoritm. The BGA may be rejected on the basis of two-dimensional information alone if it is skewed or if some of the balls are out of position with respect to the others. Because the normal image is an annulus there is very comprehensive two-dimensional information with which to make n early accept/reject decision. It is also possible to configure lighting such that the normal image is an annulus with a bright point in the center. In both cases, detecting the actual ball center is a straightforward process. The accuracy of the measurement depends on the magnification used, on the image sensor resolution, and on the robustness of the vision algorithm.

The image processor then directs capture of an oblique image using the sensor 10. Because this is arranged according to the Scheimpflug conditions, the whole of the BGA (current technology having a size of up to 45 mm) is in focus. The accuracy and speed of measurement is an improvement on conventional stereo techniques because the entire device to be inspected falls within a single field of view. The reasons for the improved accuracy are:

1. It is not necessary to build up a profile of the objects across the field as all objects are in focus in a single step image acquisition.
2. All registration information and location information in 2D and 3D can be acquired in a single instant in time during which positional errors due to moving parts and vibrations can not contribute to errors. Registration of ball position with respect to edges or fiducials is possible.
3. Complete orientation information can be obtained after the images have been acquired. There is therefore little difficulty with accurately positioning the object to be inspected within the field of view.
4. Based on the features 1 to 3 above the speed of inspection is limited only by the mechanical handling required to place the inspection object at the required location. As the entire area of the object or BGA can be imaged in a single step and full inspection performed it is not necessary to place with a high precision to orient the device. Furthermore, using strobe lighting it is not necessary to ensure that the part even remains stationary during image acquisition provided it is "relatively" stationary during the pulse (strobe) duration. Accordingly, the speed of inspection is governed by the speed of the camera. Some examples are given below.

Figure 8:
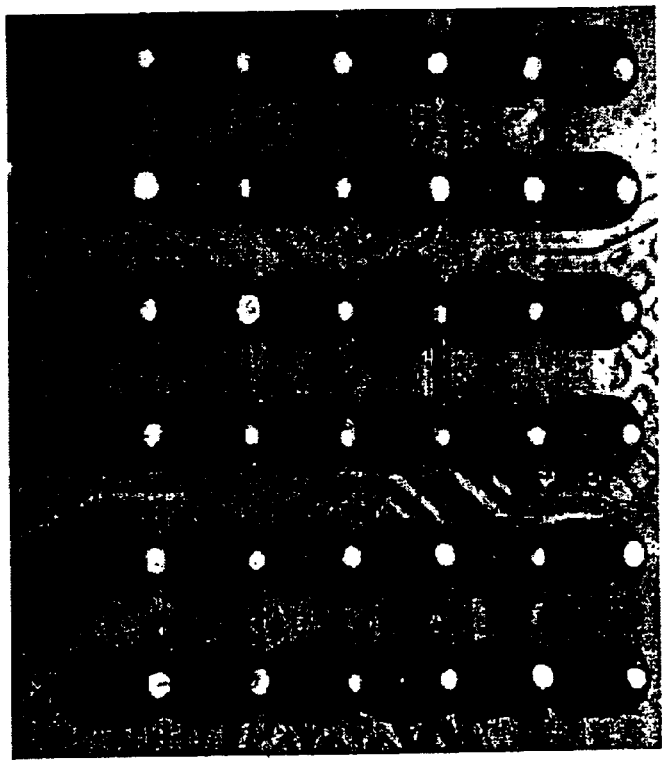
FIG. 8 is a sample image captured by an oblique camera.

The illumination used for the oblique image at the sensor 10 is that provided by the light source 31. This angle is chosen to illuminate the ball peaks, as shown in FIG. 8. The image processor 25 performs calculations to determine the geometric peak in the oblique view. The offset between this position and that of the 2D calibration view indicates the height according to the inverse function determined using the calibration procedure.

The light from the light source 30 is shut out from the sensor 10 by the filter 22 and so the annular image for each ball is not detected. This allows the images to be captured simultaneously with little post-capture image processing. The lenses used are tele-centric and so all the rays of light entering the lens are parallel with the optical axis. Hence, stray rays and reflection from other places than the top of ball are minimized. However, if non-telecentric lenses are used distortion effects can be calibrated into the measurements.

Knowing the location of each ring, a theoretical (expected) location for the reflector from the top of the ball is computed. This is achieved by searching through the LUT that was obtained during the calibration process and finding the four values that correspond to x, y locations nearest to that obtained for the ring. The exact expected location is obtained by interpolating the expected location suggested by each of the four calibration points. Also, a refined calibration value is obtained by interpolating the calibration values suggested by these four points. This will be referred to as C_CAL. Therefore, there is an expected location for the reflection in the image of the oblique camera. Any difference between this expected position and the actual position found as described above must be due to the top of the ball being at a different height with respect to the reference plane that was derived during the calibration process. This difference in height can be obtained using:

$$\text{Height} = (\text{Expected vertical location} - \text{Actual vertical location}) * C\_CAL \qquad \text{Equation 3}$$

In general, calibration requires that the coordinates of the Scheimpflug camera are related to the coordinates of the vertical camera through a calibration of the relative locations of 2D object space to the sensor pixels of each camera. This calibration step may be absolute or relative.

Using the system of the invention, it is possible to acquire an image of an entire chipscale package area and to perform complete 2D and 3D inspection without requiring multiple images. An entire device can be me measured within one field of view and both images can be acquired in a single snap. The system does not require special registration or part presentation, it only needs to be relatively still during the image acquisition or illumination time.

Also, the system is relatively insensitive to vibration, and is relatively more accurate when compared to the prior systems.

As an example, consider a 25 mm×25 mm ball grid array device. Also, consider a sensor with 1024×1280 pixels, with each pixel having dimensions of 6.7×6.7 microns (e.g. Sony ICX 085AL). Using a lens with magnification M=0.27 it is possible to image an object area of 25 microns×25 microns onto each sensor pixel. The object field of view is then 25.6 mm×32 mm and the complete BGA device may be viewed and analyzed in imaged in a single image from each camera.

Sensors with up to 2000×2000 pixels are commercially available today (e.g. Kodak KAI-4000M, 7.4 micron pixels). Using a 2000×2000 pixel sensor it is then possible to image an area of up to 54 mm×54 mm with the same lens magnification.

According to JEDEC standards, this field of view is large enough to cover all chip-scale package device sizes.

Again, considering the example of the 25 mm×25 mm BGA device above. If the handling system is designed to present the sample in any orientation the possible field of view is determined by the diagonal plus any offset due to the handler positioning error. The diagonal is approximately 36 mm. Using the 2K×2K sensor, this allows for up to +−9 mm offset in any direction. Accordingly, the mechanical constraints on positioning the devices are relaxed significantly and the possibility to achieve the frame rate of the camera is realistic.

At the other end of the range, flip chip and micro BGA devices may be as small as 5 mm×5 mm. In this situation higher resolution and accuracy is required. If higher accuracy is required larger sensors may be used or lens magnifications allowing the imaging of smaller object field features may be used. This is illustrated in the following examples.

Example 1

Returning to the example of a 25 mm BGA device. Considering a conventional vision system using a camera with a fixed exposure time of several milliseconds, a positioning system and a continuous LED lighting system, it is reasonable to present up to 8 devices per second to the vision system. Based on this and assuming the camera frame rate is greater than 8 frames per second, this corresponds to an inspection rate of 8(devices per second)×60 seconds×60 minutes=28800 devices per hour.

Example 2

Returning to the example of a 25 mm BGA device. Consider a high-speed camera system with capability of 15 frames per second and assume that the device can be presented to the camera at a rate of 15 devices per second. This corresponds to 15(frames per second)×60 seconds×60 minutes=54000 devices per hour.

Example 3

If the 25 mm BGA device mentioned above is moved on a constant feedrate conveyor with a feedrate of 1 m/s and a 1 microsecond strobe light is used as the illumination source. This will provide a 1-micron smear, which is acceptable.

Using a 30 frames per second camera allows a distance of 83 mm between devices. The inspection speed possible is then 108,000 devices per hour.

Example 4

Consider a flip chip device measuring 5 mm×5 mm and with 300 micron diameter solder balls. Using a 1024×1280 pixel camera with a pixel size of 6.7 microns and a lens with a 1:1 magnification it s possible to acquire an object field of dimensions 6.9 mm×8.6 mm. Again the full device is within a full field of view and the accuracy and resolution is improved allowing both high speed and accurate inspection where it is required for smaller samples.

The invention is not limited to the embodiments described, but may be varied in construction and detail within the scope of the claims.

What is claimed is:

1. A measurement system comprising:

means for supporting an object to be inspected in an object plane, a light source mounted to illuminate the object, an obliquely mounted camera for capture of images of the illuminated object, an image processor including means for determining height of the object using a calibration value, and, the obliquely-mounted camera includes a sensor and a separate lens, and the system further includes means for supporting the sensor and the lens of the obliquely-mounted camera at mutually different angles and forming a plane through the sensor and a plane through the lens which substantially intersect at the object plane according to the Scheimpflug principle to provide the oblique camera with a relatively large field of view in focus, the system further includes a reference camera mounted to capture a two dimensional normal image of an object, the system further includes means to move the reference and the oblique cameras or an object a known distance relative to each other, and the system includes means for generating the calibration value by capturing normal and oblique first calibration images of a two dimensional calibration tool, moving the reference and oblique cameras or the calibration tool a known distance with respect to each other in the normal z-direction, capturing normal and oblique second calibration images of the calibration tool, and the image processor determining the calibration value from said calibration images, said calibration value enabling the system to generate during use an expected location in an image from the obliquely-mounted camera for any point in an image obtained from the reference camera.

2. The measurement system as claimed in claim 1, wherein the image processor includes means for determining the calibration image from said normal image, and means for determining a centroid of the image to determine a peak of an object.

3. The measurement system as claimed in claim 2, wherein the light source is mounted with respect to the obliquely-mounted camera whereby the peak of the object is sensed.

4. The measurement system as claimed in claim 3, wherein only an area including the peak of the object is sensed.

5. The measurement system as claimed in claim 2, wherein the system further comprises a lateral light source arranged in an annular configuration with respect to the object support means to provide an annular image for the reference camera, and the image processor includes means for determining the centroid of the annular image to provide the normal image.

6. The system as claimed in claim 5, wherein the lateral light and oblique light have different wavelengths, and the light entering the camera is filtered to exclude the light for the other camera, and both the primary and the reference images are simultaneously captured.

7. The system as claimed in claim 1, wherein the object is illuminated with lateral light directed substantially parallel to the object plane with the reference image being annular, and the object is also illuminated by oblique light directed from an oblique angle with the primary image corresponds to a surface area only including an object peak.

* * * * *